United States Patent
Johnson et al.

(10) Patent No.: US 11,249,067 B2
(45) Date of Patent: Feb. 15, 2022

(54) NANOPORE FLOW CELLS AND METHODS OF FABRICATION

(71) Applicant: Applied Materials, Inc., Santa Clara, CA (US)

(72) Inventors: Joseph R. Johnson, Redwood City, CA (US); Roger Quon, Rhinebeck, NY (US)

(73) Assignee: Applied Materials, Inc., Santa Clara, CA (US)

( * ) Notice: Subject to any disclaimer, the term of this patent is extended or adjusted under 35 U.S.C. 154(b) by 201 days.

(21) Appl. No.: 16/573,540

(22) Filed: Sep. 17, 2019

(65) Prior Publication Data
US 2020/0132663 A1 Apr. 30, 2020

Related U.S. Application Data

(60) Provisional application No. 62/752,045, filed on Oct. 29, 2018.

(51) Int. Cl.
*H01L 21/00* (2006.01)
*G01N 33/487* (2006.01)
(Continued)

(52) U.S. Cl.
CPC ....... *G01N 33/48721* (2013.01); *B81B 1/004* (2013.01); *B81C 3/001* (2013.01); *B81B 2201/0214* (2013.01); *B81C 2201/019* (2013.01)

(58) Field of Classification Search
CPC ............ B81C 1/00341; B81C 1/00261; B81C 2201/019; B81C 3/001; B81C 3/004; B81B 2201/0214; B81B 1/004
See application file for complete search history.

(56) References Cited

U.S. PATENT DOCUMENTS

| 8,961,763 B2 | 2/2015 | Dunbar et al. |
| 9,194,860 B2 | 11/2015 | Peng et al. |

(Continued)

FOREIGN PATENT DOCUMENTS

| CN | 104458813 A | 3/2015 |
| CN | 104730111 A | 6/2015 |

(Continued)

OTHER PUBLICATIONS

International Search Report and Written Opinion dated Mar. 30, 2021 for Application No. PCT/US2020/063309.

(Continued)

*Primary Examiner* — Samuel A Gebremariam
(74) *Attorney, Agent, or Firm* — Patterson + Sheridan, LLP

(57) ABSTRACT

Nanopore flow cells and methods of manufacturing thereof are provided herein. In one embodiment a method of forming a flow cell includes forming a multi-layer stack on a first substrate, e.g., a monocrystalline silicon substrate, before transferring the multi-layer stack to a second substrate, e.g., a glass substrate. Here, the multi-layer stack features a membrane layer, having a first opening formed therethrough, where the membrane layer is disposed on the first substrate, and a material layer is disposed on the membrane layer. The method further includes patterning the second substrate to form a second opening therein and bonding the patterned surface of the second substrate to a surface of the multi-layer stack. The method further includes thinning the first substrate and thinning the second substrate. Here, the second substrate is thinned to where the second opening is disposed therethrough. The method further includes removing the thinned first substrate and at least portions of the material layer to expose opposite surfaces of the membrane layer.

20 Claims, 10 Drawing Sheets

(51) Int. Cl.
  *B81B 1/00*  (2006.01)
  *B81C 3/00*  (2006.01)

(56) References Cited

U.S. PATENT DOCUMENTS

| | | |
|---|---|---|
| 9,201,057 B2 | 12/2015 | Peng et al. |
| 9,696,277 B2 | 7/2017 | Dunbar et al. |
| 9,863,912 B2 | 1/2018 | Dunbar et al. |
| 10,794,895 B2 | 10/2020 | Xie |
| 10,908,121 B2 | 2/2021 | Yanagi |
| 2007/0020146 A1 | 1/2007 | Young et al. |
| 2010/0038243 A1 | 2/2010 | White et al. |
| 2010/0041246 A1 | 2/2010 | Ramappa |
| 2013/0233709 A1 | 9/2013 | Dunbar et al. |
| 2013/0263946 A1 | 10/2013 | Afzali-Ardakani et al. |
| 2014/0099726 A1 | 4/2014 | Heller |
| 2014/0131202 A1 | 5/2014 | Peng et al. |
| 2014/0131203 A1 | 5/2014 | Peng et al. |
| 2014/0174927 A1 | 6/2014 | Bashir et al. |
| 2014/0318964 A1 | 10/2014 | Dunbar et al. |
| 2016/0231307 A1 | 8/2016 | Xie |
| 2016/0266089 A1 | 9/2016 | Morin et al. |
| 2017/0269034 A1 | 9/2017 | Dunbar et al. |
| 2017/0299548 A1 | 10/2017 | Yoshida et al. |
| 2019/0094180 A1 | 3/2019 | Yanagi |
| 2020/0150084 A1 | 5/2020 | Dunbar et al. |
| 2020/0393456 A1 | 12/2020 | Alexandrakis et al. |
| 2020/0400648 A1 | 12/2020 | Xie |
| 2020/0400649 A1 | 12/2020 | Xie |

FOREIGN PATENT DOCUMENTS

| | | |
|---|---|---|
| CN | 106459869 A | 2/2017 |
| KR | 20100121303 A | 11/2010 |
| KR | 20150050770 A | 5/2015 |
| TW | 201011290 A | 3/2010 |
| WO | 2016127007 A2 | 8/2016 |
| WO | 2017165267 A1 | 9/2017 |
| WO | 2019118495 A1 | 6/2019 |

OTHER PUBLICATIONS

PCT International Search Report and Written Opinion dated Jan. 15, 2020, for International Application No. PCT/US2019/053546.

King, Sean et al., "Intrinsic stress effecton fracture toughness of plasma enhanced chemical vapor deposited SiNx: H films", Thin Solid Films, 2010, vol. 518, No. 17, pp. 4898-4907.

Ma, Hong-Ping et al., "Measurements of microstructural, chemical, optical, and electrical properties of silicon-oxygen-nitrogen films prepared by plasma-enhanced atomic layer deposition", Nanomaterials, 2018, vol. 8, No. 12, inner pp. 1-14.

International Search Report and Written Report dated Sep. 29, 2021 for Application No. PCT/US2021/036523.

Storm, A.J. et al.—"Translocation of double-strand DNA through a silicon oxide nanopore," Physical Review E 71, 051903, 2005, pp. 051903-1-051903-10.

Taiwan Office Action dated Jul. 9, 2020, for Taiwan Patent Application No. 108138553.

Search Report for Taiwan Application No. 110117685 dated Sep. 1, 2021.

NANOPORE FLOW CELLS AND METHODS OF FABRICATION

CROSS-REFERENCE TO RELATED APPLICATIONS

This application claims priority to U.S. Provisional Application Ser. No. 62/752,045, filed on Oct. 29, 2018, which is herein incorporated by reference in its entirety.

BACKGROUND

Field

Embodiments herein relate to flow cells to be used with solid-state nanopore sensors and methods of manufacturing thereof.

Description of the Related Art

Solid-state nanopore sensors have emerged as a low-cost, highly mobile, and rapid processing biopolymer, e.g., DNA or RNA, sequencing technology. Solid-state nanopore sequencing of a biopolymer strand comprises translocating the biopolymer strand through a nanoscale sized opening having a diameter between about 0.1 nm and about 100 nm, i.e., a nanopore. Typically, the nanopore is disposed through a membrane layer which separates two conductive fluid reservoirs. The biopolymer strand to be sequenced, e.g., a characteristically negatively charged DNA or RNA strand, is introduced into one of the two conductive fluid reservoirs and is then drawn through the nanopore by providing an electric potential therebetween. As the biopolymer strand travels through the nanopore the different monomer units thereof, e.g., protein bases of a DNA or RNA strand, occlude different percentages of the nanopore thus changing the ionic current flow therethrough. The resulting current signal pattern can be used to determine the sequence of monomer units in the biopolymer strand, such as the sequence of proteins in a DNA or RNA strand.

Often, the membrane layer and the nanopore disposed therethrough are fabricated on a monocrystalline silicon substrate which together therewith forms a nanopore flow cell. The monocrystalline silicon substrate is typically the same or similar to substrates used in the manufacturing of semiconductor devices. Using the same or similar substrate to those used in the manufacture of semiconductor devices facilitates fabrication of the nanopore flow cell using commercially available semiconductor device manufacturing equipment and methods.

Typically, a membrane layer is deposited onto a front side surface of a silicon substrate and the nanopore opening is formed through the membrane layer, but not through the silicon substrate, using a photolithography patterning and etch processing sequence. A surface of the membrane layer disposed proximate to the silicon substrate is then exposed by etching an opening into a backside surface of the silicon substrate. Typically, the opening in the backside surface of the silicon substrate is formed by exposing the backside surface of the substrate to a wet or aqueous silicon etchant, such as KOH, through a patterned mask disposed thereon. A typical silicon substrate will need to be exposed to the silicon etchant for between 9 and 13 hours to anisotropically etch through the thickness thereof. This long etch time undesirably increases the cycle time, and thus the cost, of forming the nanopore flow cell. Further, charges accumulated in the monocrystalline substrate used to support the membrane layer during high frequency nucleotide detection in a conventional nanopore flow cell undesirably increase background noise in the current signal. This undesirable background noise reduces the detection resolution of the nanopore sensor or flow cell.

Accordingly, what is needed in the art are improved methods of forming a nanopore flow cell for use in a solid-state nanopore sensor and improved nanopore flow cells formed therefrom.

SUMMARY

Embodiments of the present disclosure provide devices, e.g., nanopore flow cells, which may be used in a solid-state nanopore sensor, and methods of manufacturing thereof.

In one embodiment a method of forming a flow cell includes forming a multi-layer stack on a first substrate, e.g., a monocrystalline silicon substrate, before transferring the multi-layer stack to a second substrate, e.g., a glass substrate. Here, the multi-layer stack features a membrane layer, having a first opening formed therethrough, where the membrane layer is disposed on the first substrate, and a material layer is disposed on the membrane layer. The method further includes patterning the second substrate to form a second opening therein and bonding the patterned surface of the second substrate to a surface of the multi-layer stack. The method further includes thinning the first substrate. The method further includes removing the thinned first substrate and at least portions of the first and second material layers to expose opposite surfaces of the membrane layer. In some embodiments, the second opening is disposed through the second substrate. In other embodiments, the method includes thinning the second substrate to where the second opening is disposed therethrough. Here, the second substrate may be thinned before or after the patterned surface thereof is bonded to the surface of the multi-layer stack.

In another embodiment, a method of forming a flow cell includes forming a multi-layer stack on a first substrate, the multi-layer stack comprising a membrane layer interposed between a first material layer and a second material layer, where the membrane layer features a first opening formed therethrough. The method further includes patterning a surface of a second substrate to form a second opening therein, bonding the patterned surface of the second substrate to a first surface of the multi-layer stack, and removing the first substrate from the multi-layer stack to expose a second surface of the multi-layer stack opposite of the first surface. The method further includes patterning a surface of a third substrate to form a third opening therein, bonding the patterned surface of the third substrate to the second surface of the multi-layer stack, and thinning the second substrate and the third substrate to where the second opening and the third openings are respectively disposed therethrough. The method further includes removing at least portions of the first and second material layers to expose opposite surfaces of the membrane layer.

In another embodiment a nanopore flow cell features a glass substrate having an opening formed therethrough and a membrane layer disposed on the glass substrate. The membrane layer features a single nanopore disposed therethrough. The single nanopore is located in a portion of the membrane layer which spans the opening formed through the glass substrate.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements and features of one aspect may be beneficially incorporated in other aspects without further recitation.

DETAILED DESCRIPTION

Embodiments of the present disclosure provide devices, e.g., nanopore flow cells, which may be used in a solid-state nanopore sensor, and methods of manufacturing the same. The methods described herein generally include forming a patterned multi-layer stack on a sacrificial monocrystalline silicon substrate before transferring the patterned multi-layer stack to a host substrate. The patterned multi-layer stack typically features a membrane layer having a nanoscale opening disposed therethrough. The host substrate is typically formed of a dielectric glass material. Thus, the nanopore flow cells formed herein are substantially free of monocrystalline silicon materials. Beneficially, the glass material of the host substrate eliminates or substantially reduces background noise levels associated with solid-state nanopore flow cells comprising a monocrystalline silicon substrate.

Figure 1:
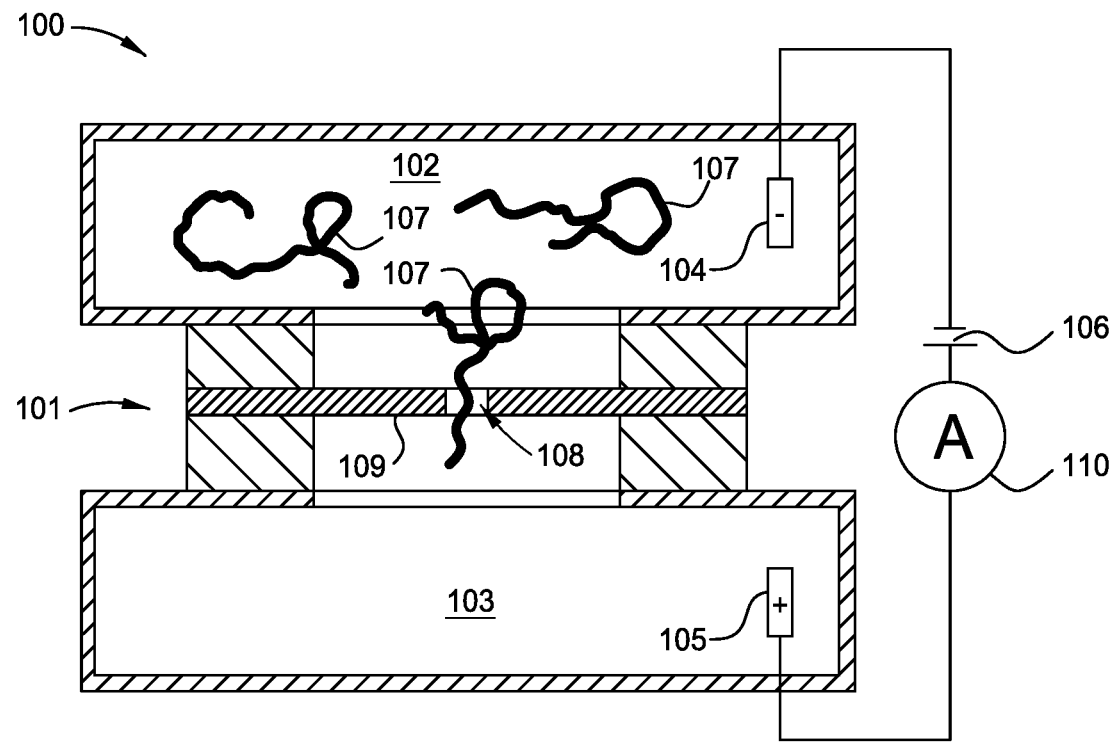
FIG. 1 is a schematic cross-sectional view of a nanopore sensor, according to one embodiment.

FIG. 1 is a schematic cross-sectional view of a nanopore sensor 100 which may be used to sequence a biopolymer strand, according to one embodiment. Here, the nanopore sensor 100 features a flow cell 101 interposed between a first reservoir 102 and a second reservoir 103. Here, each of the first and second reservoirs 102, 103 an electrically conductive fluid and a respective electrode 104, 105 which is in communication with a voltage source 106. The voltage source 106 is used to produce an ionic current flow from the first reservoir 102 to the second reservoir 103 through a single nanoscale sized opening, here the nanopore 108. The nanopore 108 is disposed through a dielectric membrane layer 109 of the flow cell 101.

Here, the ionic current flow draws a characteristically negatively charged DNA or RNA biopolymer strand, e.g. one of the biopolymer strands 107 from the first reservoir 102 through the nanopore 108 and into the second reservoir 103. As the biopolymer strand 107 is drawn through the nanopore 108 the monomer units thereof sequentially occlude the nanopore 108 causing a change in the ionic current flow therethrough. Typically, the change in the ionic current flow corresponds to a characteristic, such as a dimension or charge, of the monomer unit simultaneously passing through the nanopore 108. Here, the ionic current flow and changes in the ionic current flow are measured using an ion current sensor, such as a pico ammeter 110.

Figure 2:
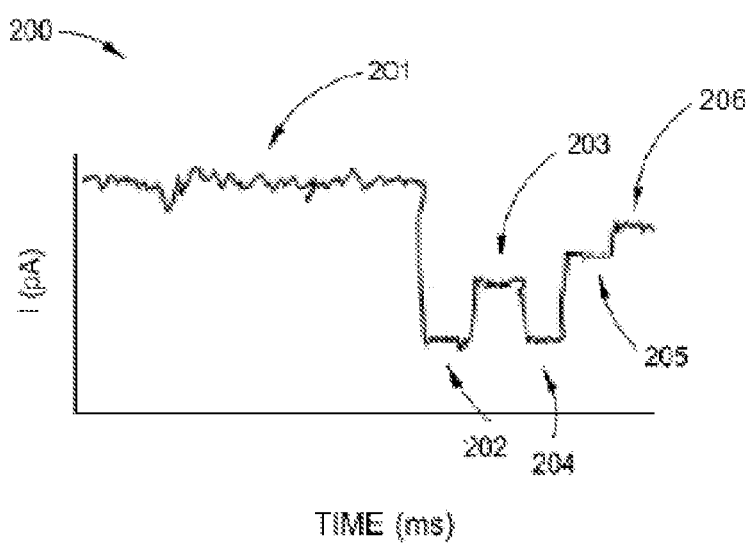
FIG. 2 is a graph illustrating the ionic current flow through a nanoscale sized opening, such as the nanopore described in FIG. 1, as a biopolymer strand is drawn therethrough.

FIG. 2 is a graph 200 illustrating the ionic current flow through a nanoscale sized opening, such as the nanopore 108 described in FIG. 1, as a biopolymer strand or portion thereof, e.g., a DNA strand or RNA strand, passes therethrough. Here, the graph 200 shows a baseline value 201 where no biopolymer strand is occluding the opening and ionic current flows freely therethrough. As the biopolymer strand is drawn into the nanopore, a monomer unit thereof occludes a portion of the nanopore causing the ionic current flow to change to a first value 202. As successive monomer units occlude the nanopore, i.e., as the biopolymer strand is drawn further therethrough, the ionic current flow changes to corresponding values 203-206 which are dependent on the percentage of the cross-sectional area of the nanopore occluded by the biopolymer strand. The sequential values 202-206 corresponding to monomer units of the biopolymer strand can thus be used to determine a monomer unit sequence, e.g., a DNA or RNA base sequence, of the biopolymer strand.

Figure 3:
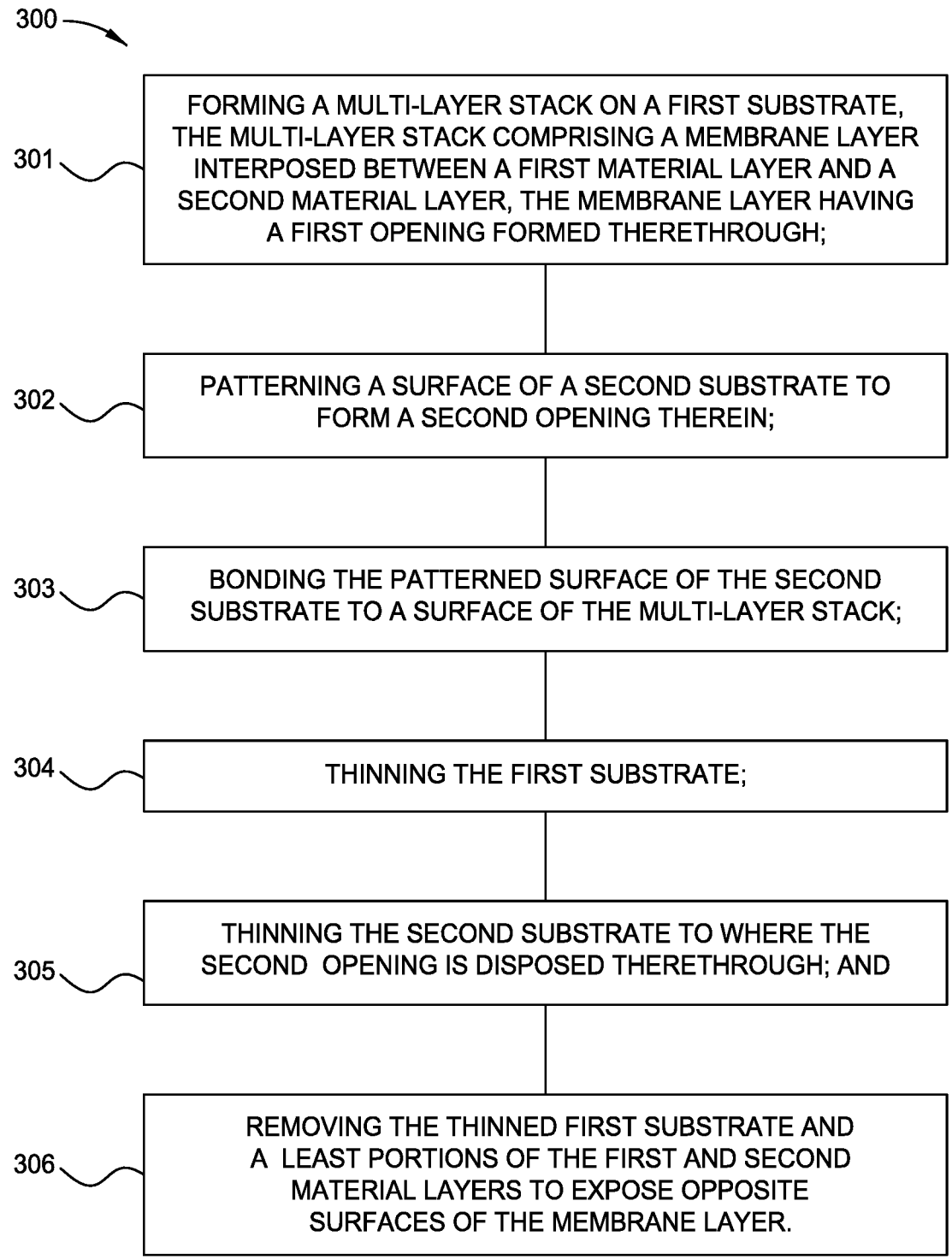
FIG. 3 is a flow diagram setting forth a method of forming a nanopore flow cell, according to one embodiment.

FIG. 3 is a flow diagram setting forth a method 300 of forming a nanopore flow cell, according to one embodiment. FIGS. 4A-4I illustrate various aspects of the method 300 set forth in FIG. 3.

Figure 4A:
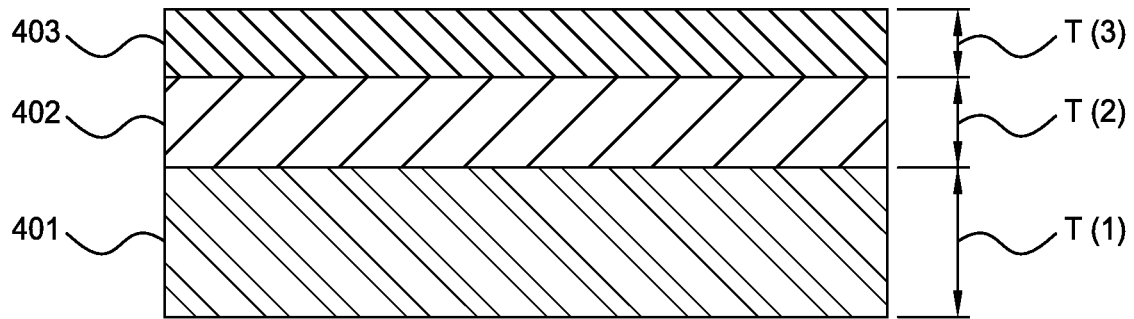
FIGS. 4A-4I illustrate various aspects of the method set forth in FIG. 3.

At activity 301 the method 300 includes forming a multilayer stack on a first substrate 401, shown in FIG. 4A. The multi-layer stack features a membrane layer 403 interposed between a first material layer 402 and a second material layer 405. The membrane layer 403 has a first opening 404, e.g., a single nanopore, formed therethrough. Typically, the first substrate 401, is formed of monocrystalline silicon and has a thickness $T(1)$. The thickness $T(1)$ is selected to facilitate handling and processing of the first substrate 401 using the same or similar equipment and methods used for processing silicon substrates in a semiconductor device manufacturing facility. In some embodiments, the first substrate 401 has a thickness $T(1)$ of between about 450 μm and about 800 μm, such as between about 600 μm and about 800 μm, for example between about 700 μm and about 800 μm.

Figure 4B:
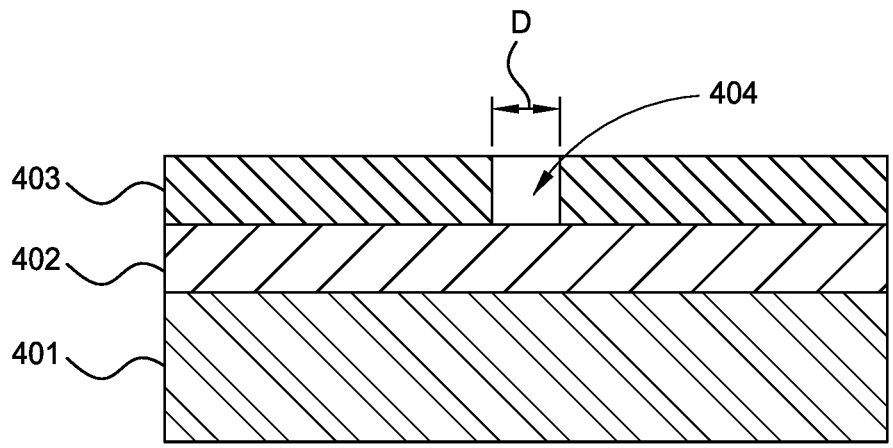
Figure 4C:
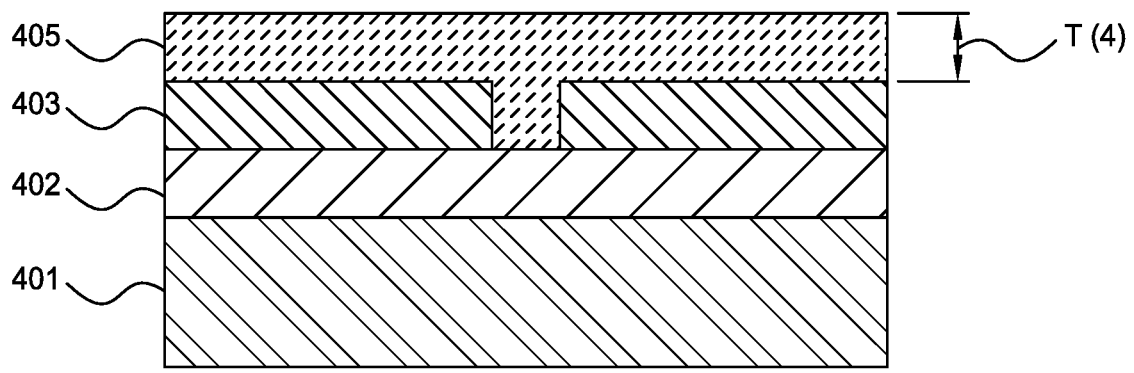

Here, forming the multi-layer stack includes depositing the first material layer 402 onto the first substrate 401, depositing a membrane layer 403 over the first material layer 402, and patterning the membrane layer 403 to form a first opening 404 therethrough, such as shown in FIGS. 4A-4B. In some embodiments, forming the multi-layer stack further includes depositing the second material layer 405 over the membrane layer 403, such as shown in FIG. 4C In some embodiments, the multi-layer stack does not include the first material layer 402. In those embodiments, the multi-layer stack includes the membrane layer 403, deposited onto the first substrate 401, and the second material layer 405 deposited onto the membrane layer 403.

Typically, the first material layer 402 is formed of a dielectric material, such as a silicon oxide ($Si_xO_y$), for example $SiO_2$. Here, the first material layer 402 is deposited to a thickness T(2) of more than about 10 nm, such as between about 10 nm and about 500 nm, between about 10 nm and 400 nm, between about 10 nm and about 300 nm, for example between about 10 nm and about 200 nm. In other embodiments, the first material layer 402 is deposited to a thickness T(2) of more than about 1 μm, such as more than about 2 μm, or more than about 3 μm, for example between about 4 μm and about 6 μm.

The membrane layer 403 is formed of a dielectric material which is different from the dielectric material(s) used to form the first and second material layers 402, 405. For example, in some embodiments the membrane layer 403 is formed of a silicon nitride or silicon oxynitride material, such as $Si_xN_y$ or $SiO_xN_y$. Typically, the membrane layer 403 is deposited to a thickness T(3) of about 500 nm or less, such as about 400 nm or less, about 300 nm or less, about 200 nm or less, about 100 nm or less, or about 50 nm or less, for example between about 0.1 nm and about 100 nm or between about 1 nm and about 100 nm.

The first opening 404 is formed to extend through the membrane layer 403 and to have a diameter D of less than about 100 nm, such as less than about 50 nm, or between about 0.1 nm and about 100 nm, for example between about 1 nm and about 100 nm, or between about 0.1 nm and about 50 nm. Here, the first opening 404 is formed using one or a combination of suitable lithography and material etching patterning methods. Typically, suitable lithography methods include nanoimprint lithography, directed self-assembly, photolithography, ArF laser immersion lithography, deep UV lithography, or combinations thereof.

Here, the second material layer 405, deposited over the membrane layer 403, is formed of a dielectric material which may be the same or different from the dielectric material used to form the first material layer 402. In some embodiments, the second material layer 405 is deposited to a thickness T(4) of between about 10 nm, such as between about 10 nm and about 500 nm, between about 10 nm and 400 nm, between about 10 nm and about 300 nm, for example between about 10 nm and about 200 nm. Herein, the layers of the multi-layer stack may be formed using any suitable deposition method. For example, in some embodiments, the layers of the multi-layer stack are deposited using one, or a combination, of chemical vapor deposition (CVD) or physical vapor deposition (PVD) methods.

Figure 4D:
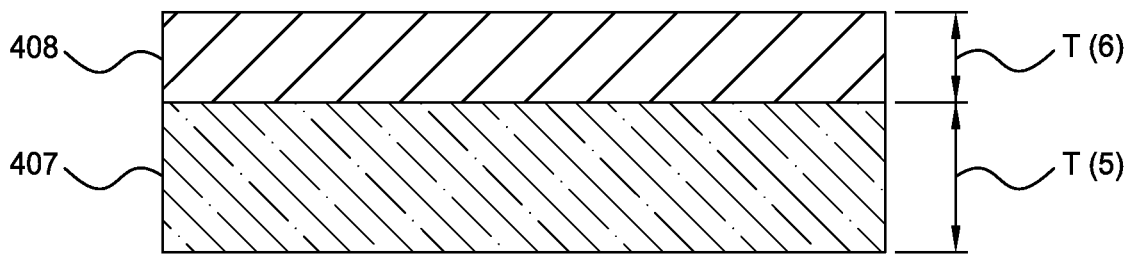
Figure 4E:
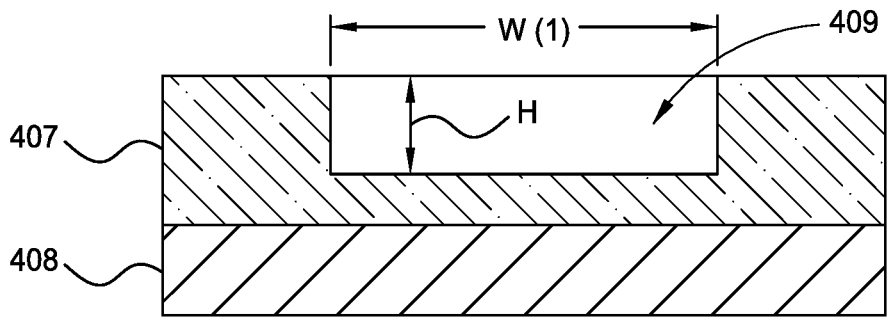

At activity 302 the method 300 includes patterning a surface of a second substrate 407 to form an opening therein, here the second opening 409 shown in FIGS. 4D-4E. Typically, the second substrate 407 is formed of dielectric material having a thickness T(5) selected to facilitate handling and processing of the second substrate 407 using the same or similar equipment used for processing silicon substrates in a semiconductor device manufacturing facility. For example, in some embodiments, the second substrate 407 has a thickness T(5) of between about 450 μm and about 800 μm, such as between about 600 μm and about 800 μm, for example between about 700 μm and about 800 μm. In other embodiments, the second substrate 407 has a thickness of about 400 μm or less, such as about 300 μm or less, for example about 300 μm.

Here, the second substrate 407 is formed for example of a non-crystalline amorphous solid, i.e., glass, such as a transparent silica-based glass material, for example a fused silica i.e., an amorphous quartz material, or a borosilicate glass material. In some embodiments, the second substrate 407 has an opaque material layer 408, for example an amorphous silicon layer, deposited on a backside surface thereof. The backside surface of the second substrate 407 is opposite of the surface to be patterned, here the front side surface into which the second opening 409 is formed. When used, the opaque material layer 408 typically has a thickness T(6) of about 20 nm or more, for example about 100 nm or more. The opaque material layer 408 facilitates the detection of an otherwise optically transparent substrate, according to some embodiments, by optical sensors of conventional semiconductor device manufacturing equipment.

Here, the second opening 409 is formed to extend from a surface of the second substrate 407, here the patterned surface, to a depth H of between about 100 μm or more and less than the thickness T(5) of the second substrate 407. For example, in some embodiments, the depth H of the second opening 409 extends between about 100 μm and about 600 μm, or between about 200 μm and about 400 μm, from the front side surface of the second substrate 407. In some other embodiments, such as in embodiments where the thickness of the second substrate 407 is less than about 400 μm the second opening 409 is formed to extend through the thickness of thereof.

Here, the second opening 409 is formed to have a width W(1) of between about 1 μm and about 20 μm, such as between about 1 μm and about 15 μm, between about 5 μm and about 15 μm, or between about 5 μm and about 10 μm. The second opening 409 may be formed using any suitable combination of photolithography and material etching patterning methods.

Figure 4F:
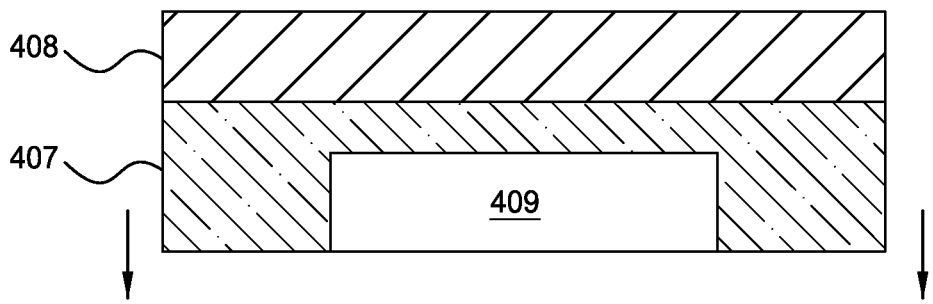
Figure 4F:
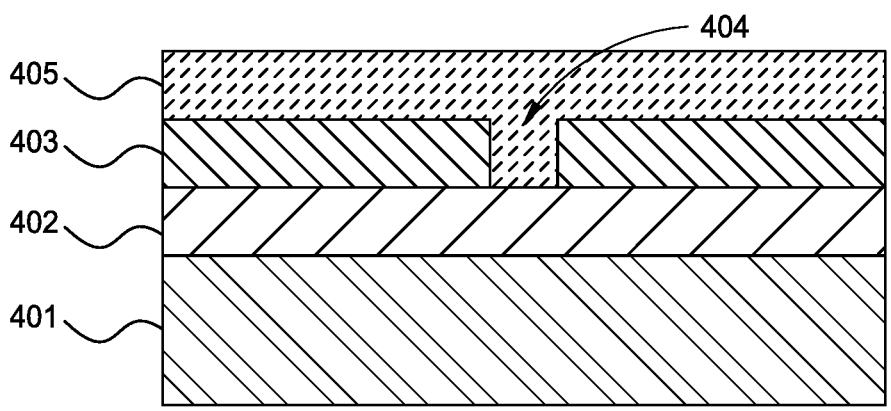
Figure 4G:
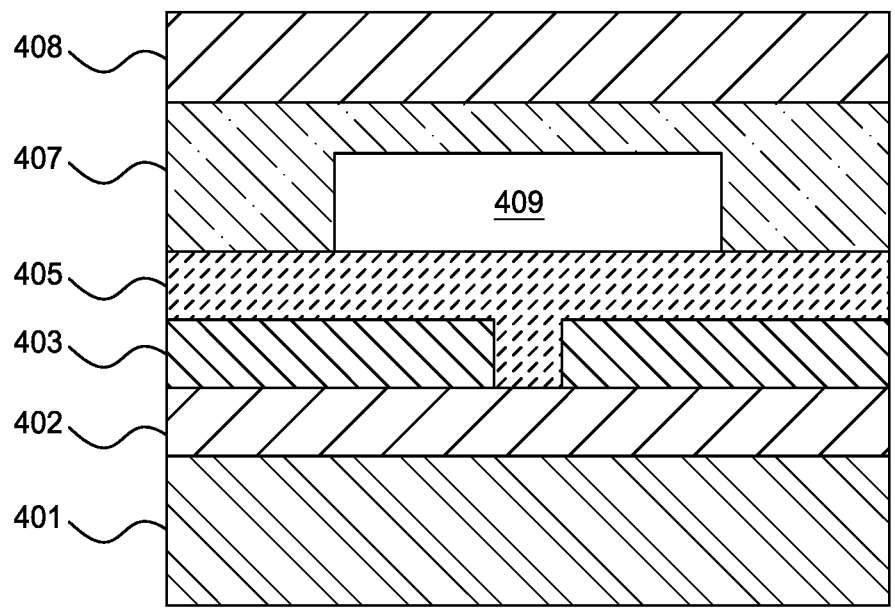
Figure 4H:
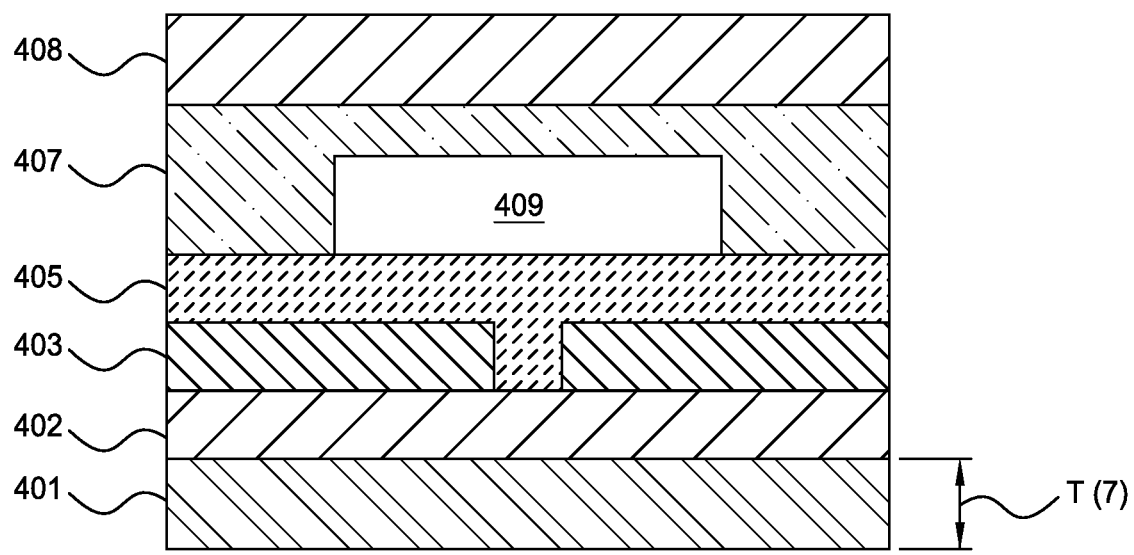

At activity 303 the method 300 includes bonding the patterned surface of the second substrate 407 to an exposed surface of the multi-layer stack disposed on the first substrate 401, such as shown in FIGS. 4F-4G. Typically, the patterned surface of the second substrate 407 and the exposed surface of the multi-layer stack are bonded together using a suitable direct bonding method. Direct bonding describes methods of joining two substrate surfaces at an atomic level, e.g., through chemical bonds between the substrates, without the use of intermediate layers, such as conductive adhesive layers, solders, etc., interposed therebetween. In one example, a suitable direct bonding method includes plasma activating one or both of the surfaces to be bonded of the substrates 401, 407, contacting the surfaces to be bonded, applying a compressive bonding force to the contacted substrates to form a composite substrate, and annealing the composite substrate.

Herein, bonding the patterned surface of the second substrate 407 to the exposed surface of the multi-layer stack includes aligning the second opening 409 407 with the first opening 404. When the first and second substrates 401, 407 are properly aligned, the first opening 404 and the second opening 409 in the resulting nanopore flow cell will be in fluid communication, e.g., a portion of the membrane layer 403 having the first opening 404 formed therethrough will span the second opening 409 formed in the second substrate 407.

At activity 304 the method 300 includes thinning the first substrate 401. Thinning the first substrate 401 includes any one or combination of grinding, lapping, chemical mechanical planarization (CMP), etching, or cleaving methods which may be used to achieve a desired thickness T(7) (shown in FIG. 4H). In embodiments where the thinning the first substrate 401 comprises a cleaving method, a surface of the first substrate 401 is typically implanted with one or a combination of hydrogen or helium ions to a depth of about 100 nm before forming the multi-layer stack thereon. The implant process desirably introduces a layer of damage, e.g., microbubbles, into the first substrate 401 to facilitate cleaving of the first substrate 401 along the damaged layer. Typically, the first substrate 401 is thinned to a thickness T(7) of less than about 100 µm, such as less than about 50 µm, less than about 10 µm, or for example less than about 1 µm. In some embodiments, the first substrate 401 is thinned to a thickness T(7) less than about 500 nm, such as less than about 200 nm, for example about 100 nm or less.

Figure 4I:
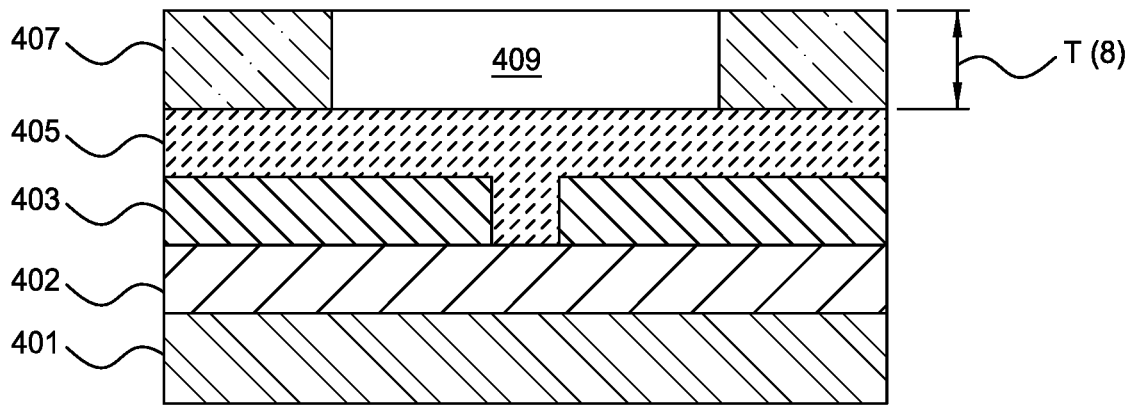

At activity 305 the method 300 includes thinning the second substrate 407 using any one or combination of grinding, lapping, CMP, or etching methods to achieve a desired thickness T(8) (shown in FIG. 4I). Here, the second substrate 407 is thinned until the second opening 409 is disposed therethrough, i.e., the thickness T(8) is the same or less than the depth H of the second opening 409 formed in the patterned surface at activity 302. For example, in some embodiments the thickness T(8) of the thinned second substrate 407 is less than about 700 µm, such as less than about 600 µm, less than about 500 µm, for example less than about 400 µm or between about 100 µm and about 700 µm, such as between about 200 µm and about 500 µm. In some embodiments, the second substrate 407 is thinned before the patterned surface thereof is bonded to the surface of the multi-layer stack.

Figure 4J:
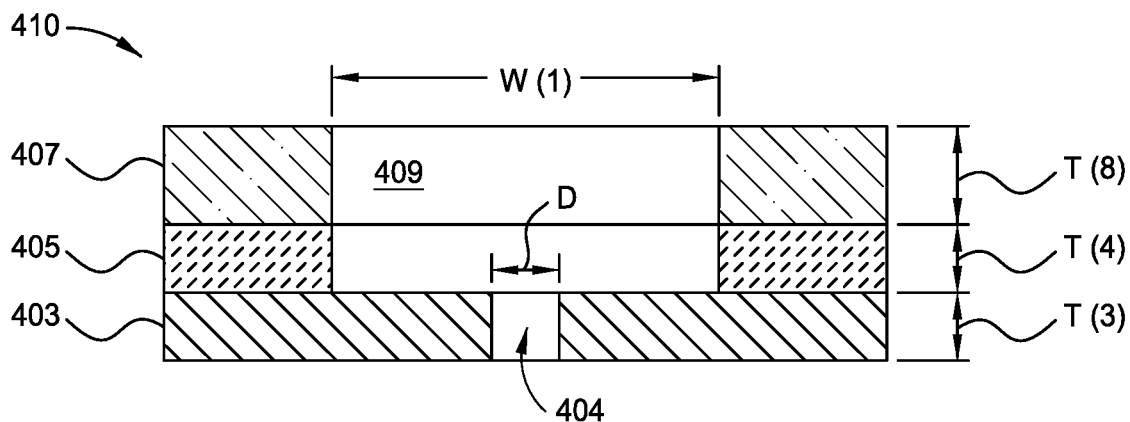
FIG. 4J is a schematic cross sectional view of a nanopore flow cell formed according to one embodiment of the method set forth in FIG. 3.
Figure 4K:
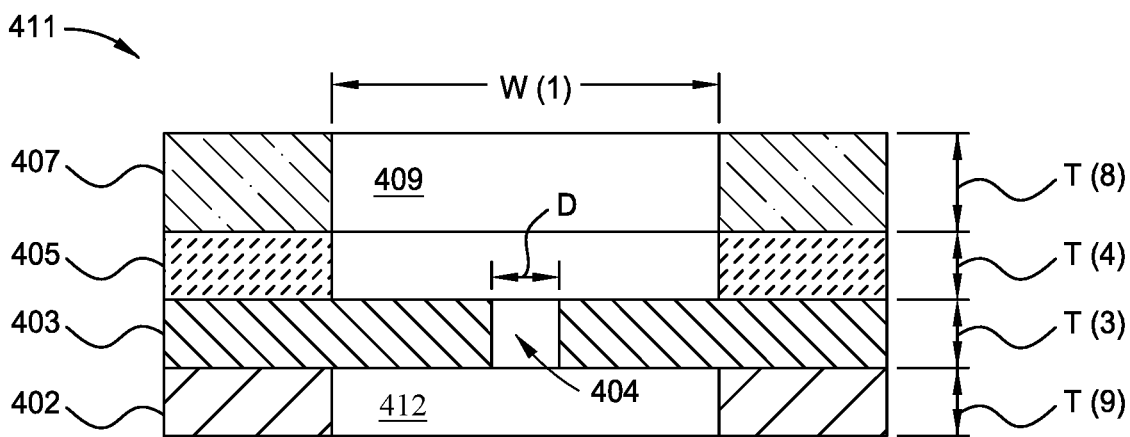
FIG. 4K is a schematic cross sectional view of a nanopore flow cell formed according to another embodiment of the method set forth in FIG. 3.

At activity 306 the method 300 includes removing the thinned first substrate 401 and at least portions of the first and second material layers 402, 405 to expose opposite surfaces of the membrane layer 403 spanning the second opening 409, such as shown in FIG. 4J or 4K. In some embodiments, removing the thinned first substrate 401 and at least portions of the first and second material layers 402, 405 includes exposure thereof to a wet or aqueous etchant, such as KOH or a combination of KOH and HF.

In some embodiments, such as shown in FIG. 4J, all or substantially all of the first material layer 402 is removed from the surface of the membrane layer 403 disposed distal from the second substrate 407. In other embodiments, such as shown in FIG. 4K, a third opening 412 is formed in the first material layer 402 and a surface of the membrane layer 403 is exposed therethrough. The third opening 412 may be formed using any suitable combination of photolithography and material etching patterning methods, e.g., a plasma assisted etching or a wet etching (aqueous solution) process.

FIG. 4J is a schematic cross sectional view of a flow cell 410, formed according to the method set forth in FIG. 3, which may be used in place of the flow cell 101 described in FIG. 1. Here, the flow cell 410 includes the second substrate 407, having the thickness T(8), and the second material layer 405, having the thickness T(4), disposed on the second substrate 407. The second opening 409, having the width W(1), is disposed through the second substrate 407 and further through the second material layer 405. The membrane layer 403, having the thickness T(3) and the first opening 404 disposed therethrough, is disposed on the second material layer 405 and spans the second opening 409. Here, the first opening 404 is in fluid communication with the second opening 409.

FIG. 4K is a schematic cross sectional view of a nanopore flow cell 411, formed according to the method set forth in FIG. 3, which may be used in place of the flow cell 101 described in FIG. 1. Here, the flow cell 411 is substantially the same as the flow cell 410 described in FIG. 4J and further includes the first material layer 402 disposed on the membrane layer 403, the first material layer 402 having an opening, here the third opening 412, disposed therethrough. Here, a thickness T(9) of the first material layer 402 is between about 1 µm and about 5 µm. In some embodiments, a width of the third opening 412 is the same as the width W(1) of the second opening 409. In other embodiments the width of the third opening 412 is less than or more than the width W(1) of the second opening 409. Here, the third opening 412 is in fluid communication with the second opening 409 and the first opening 404 is disposed therebetween.

Figure 5:
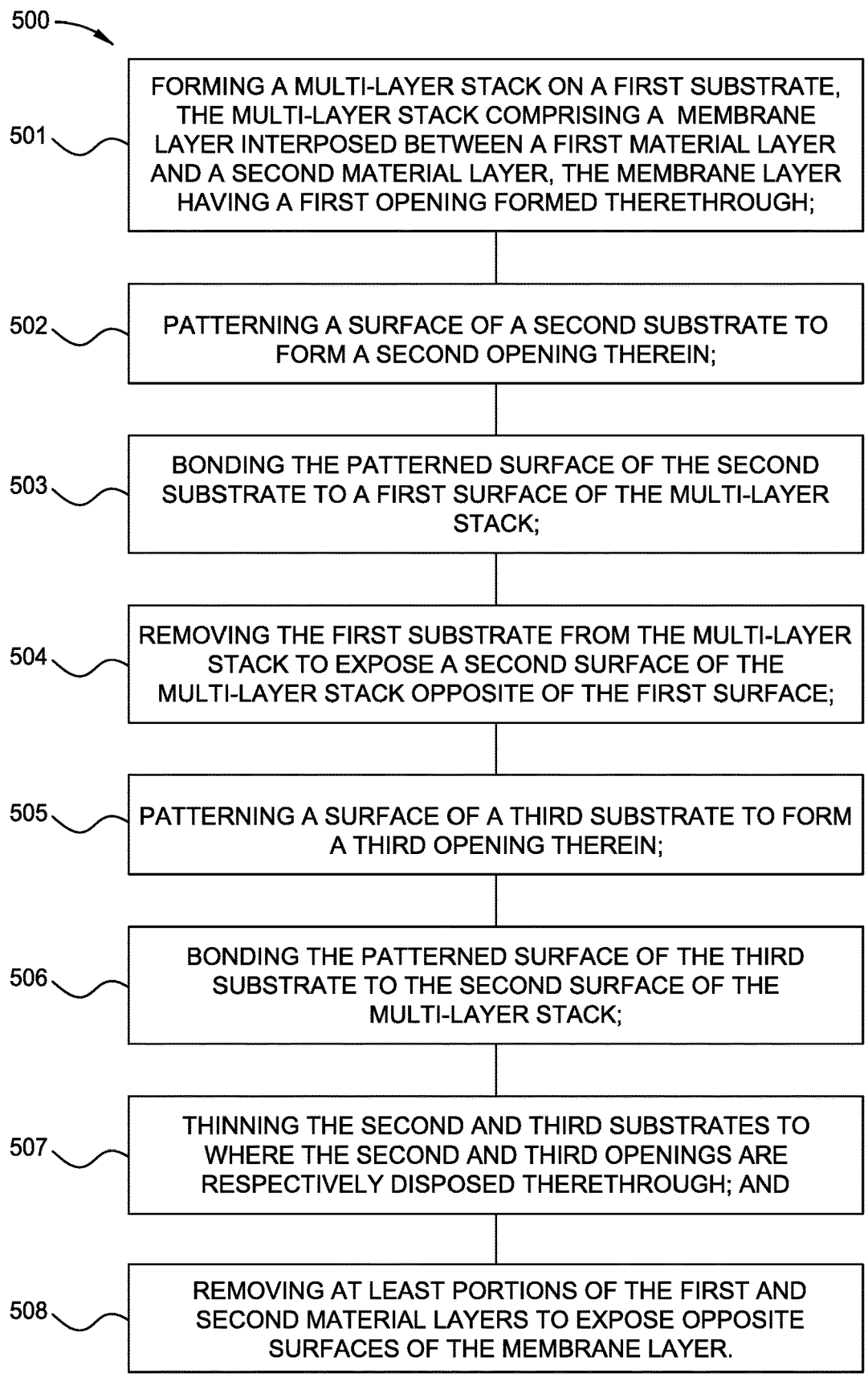
FIG. 5 is a flow diagram setting forth a method of forming a nanopore flow cell, according to another embodiment.
Figure 6A:
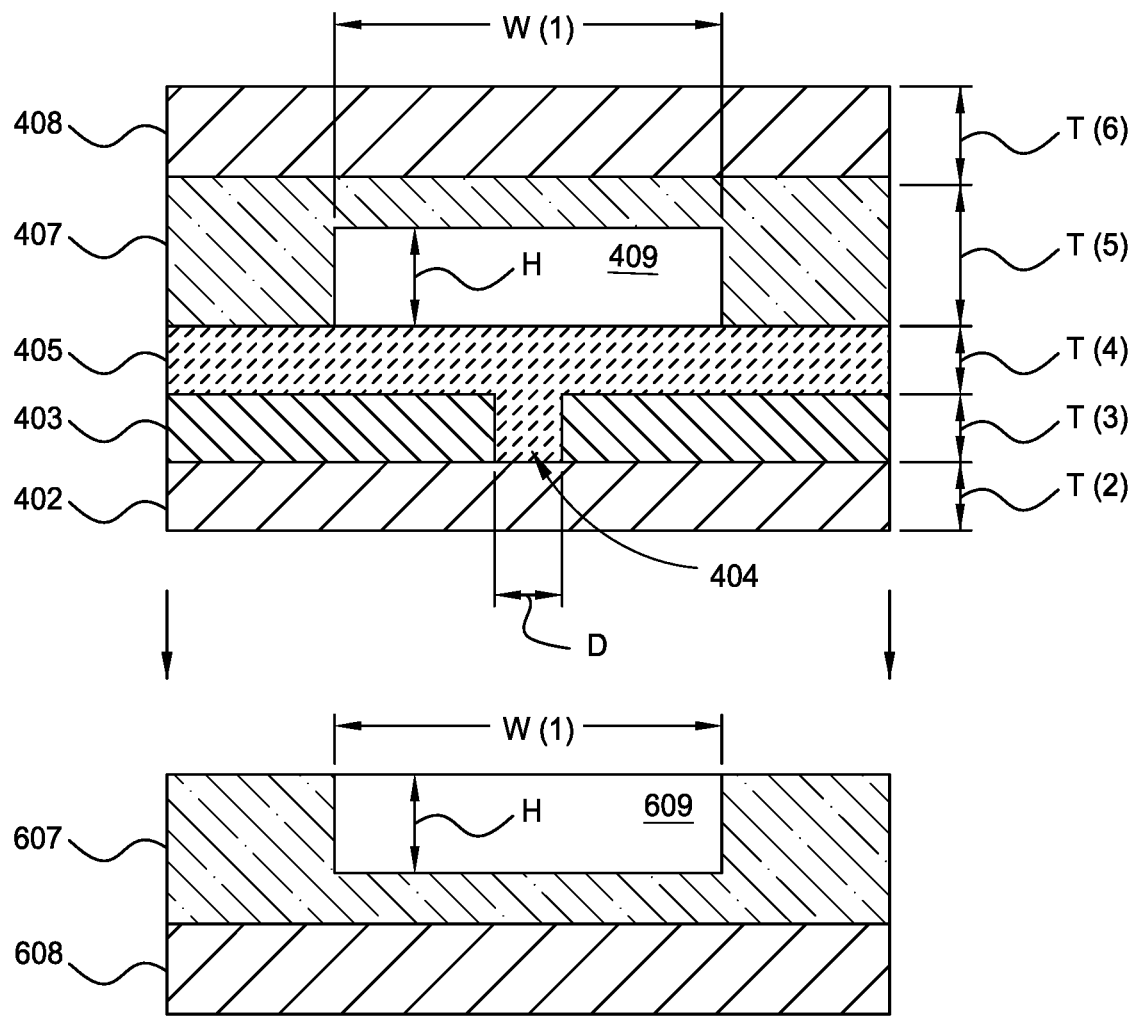
FIGS. 6A-6C illustrate various aspects of the method set forth in FIG. 5.
Figure 6B:
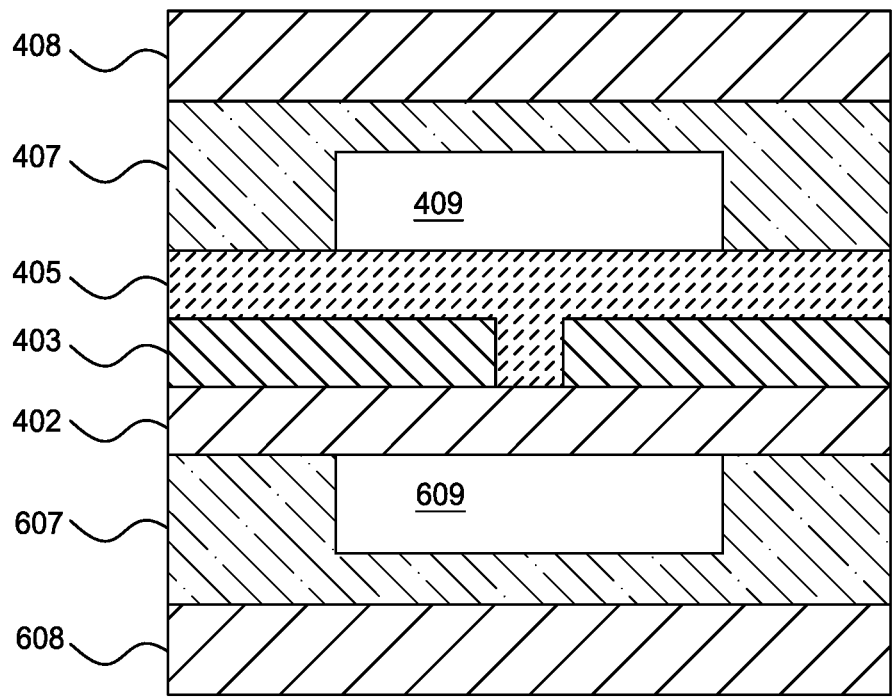
Figure 6C:
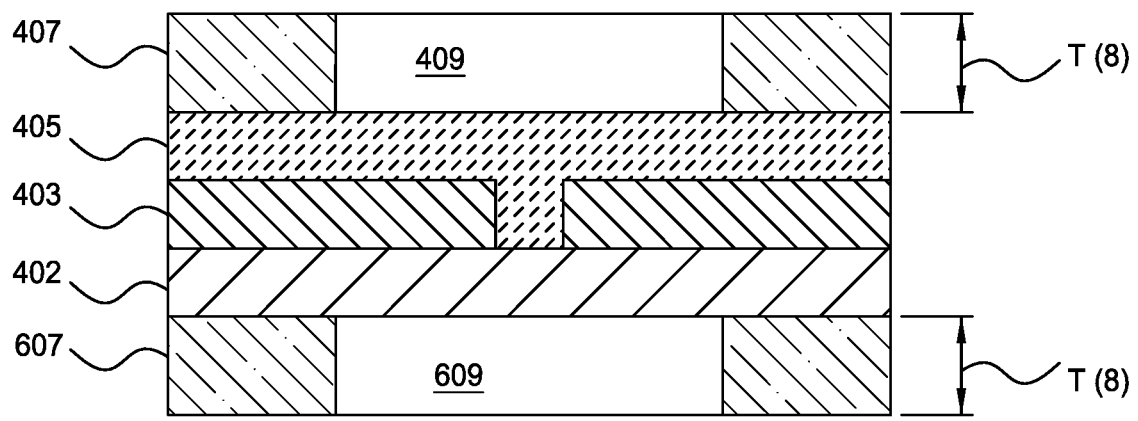

FIG. 5 is a flow diagram setting forth a method of forming a flow cell, according to another embodiment. FIGS. 6A-6C illustrate various aspects of the method set forth in FIG. 5 in addition to the aspects illustrated in FIGS. 4A-4H.

Here, activities 501-502 of the method 500 are the same as activities 301-302 of the method 300 set forth in FIG. 3, illustrated in FIGS. 4A-4E, and described above.

Activity 503 of the method 500 includes bonding the patterned surface of the second substrate 407 to an exposed surface of the multi-layer stack, here a first surface, such as described in activity 303 of the method 300 set forth in FIG. 3 and illustrated in FIG. 4F.

At activity 504 the method 500 includes removing the first substrate 401 from the multi-layer stack to expose a second surface of the multi-layer stack. Here, the second surface of the multi-layer stack is opposite of the first surface and is disposed proximate to the first substrate 401 before the first substrate 401 is removed therefrom. Removing the first substrate 401 from the multi-layer stack may include any one or combination of grinding, lapping, chemical mechanical planarization (CMP), etching, or cleaving methods described in activity 304 of the method 300 set forth in FIG. 3.

At activity 505 the method 500 includes patterning a surface of a third substrate, such as the third substrate 607 shown in FIG. 6A, to form an opening therein, here the third opening 609. In some embodiments, the third substrate 607 is formed of the same dielectric material used to form the second substrate 407 and has the same or substantially the same thickness T(5). In some embodiments, the third substrate 607 is patterned using the methods of patterning the second substrate 407 described in activity 302 of the method 300. In some embodiments, the opening 609 is formed to have the same width W(1) and depth H as the second opening 409 in the second substrate 407. In some embodiments, the third substrate 607 includes an opaque material layer 608 deposited on a backside surface thereof. In some embodiments, the opaque material layer 608 is formed of the same material and has the same thickness T(6) as the opaque material layer 408 disposed on the second substrate 407. In other embodiments, the third substrate 607 is formed of a dielectric material which is different than the dielectric material of the second substrate 407, patterned using a different method than the methods set forth in activity 302 of the method 300, and/or the opening is formed to have a different width and depth than the width W(1) and depth H of the second opening 409.

At activity 506 the method 500 includes bonding the patterned surface of the third substrate 607 to the second surface of the multi-layer stack using a suitable direct bonding method. A suitable direct bonding method is described at activity 303 of the method 300 set forth in FIG. 3. Herein, bonding the patterned surface of the third substrate 607 to the second surface of the multi-layer stack includes aligning the third opening 609 formed in third substrate 607 with the first opening 404 formed in the membrane layer 403, such as shown in FIGS. 6A-6B.

At activity 507 the method 500 includes thinning the second and third substrates 407, 607 to thickness T(8) where the second and third openings 409, 609 are respectively disposed therethrough. Typically, thinning the second and third substrates 407, 607 includes any one or combination of grinding, lapping, CMP, or etching methods to achieve the desired thickness T(8), shown in FIG. 6C, which may be the same or different for each of the second and third substrates 407, 607 respectively.

Figure 6D:
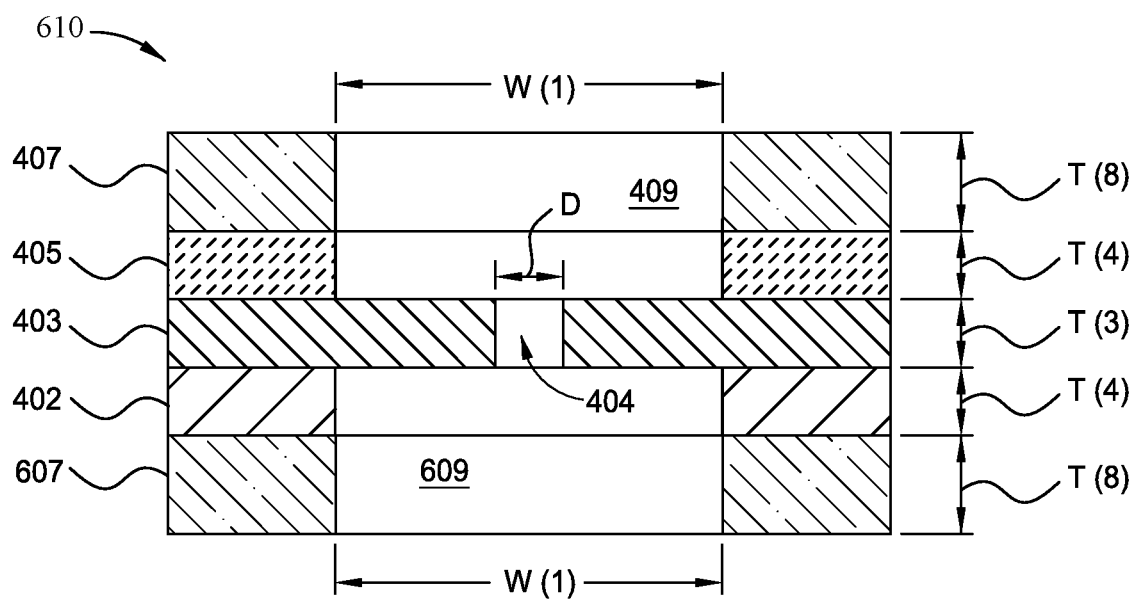
FIG. 6D is a schematic cross sectional view of a nanopore flow cell formed according to one embodiment of the method set forth in FIG. 5.

At activity 508 the method 500 includes removing at least portions of the first and second material layers 402, 405 to expose opposite surfaces of the membrane layer 403, such as shown in FIG. 6D. In some embodiments, removing the at least portions of the first and second material layers 402, 405 comprises exposure thereof to an etchant, such as KOH or a combination of KOH and HF.

FIG. 6D is a schematic cross sectional view of a flow cell 610 formed using the method set forth in FIG. 5, which may be used in place of the flow cell 101 described in FIG. 1. Here, the flow cell 610 is substantially the same as the flow cell 410 described in FIG. 4J and further includes the first material layer 402, having the thickness T(4), disposed on the membrane layer 403, and the third substrate 607 disposed on the first material layer 402. Here, the third substrate 607 has a thickness which is the same and the thickness T(8) of the second substrate 407. In other embodiments, the thicknesses of the second and third substrates 407, 607 are different. The third opening 609 is disposed through the third substrate 607 and further through the first material layer 402. A width of the third opening 609 is the same as the width W(1) of the second opening 409. In other embodiments the width of the third opening 609 is less than or more than the width W(1) of the second opening 409. In embodiments herein, the third opening 609 is in fluid communication with the first opening 404 and the second opening 409.

While the foregoing is directed to embodiments of the present disclosure, other and further embodiments of the disclosure may be devised without departing from the basic scope thereof, and the scope thereof is determined by the claims that follow.

The invention claimed is:

1. A method of forming a flow cell, comprising:
    forming a multi-layer stack on a first substrate, the multi-layer stack comprising a membrane layer disposed on the first substrate and a material layer disposed on the membrane layer, the membrane layer having a first opening formed therethrough;
    patterning a surface of a second substrate to form a second opening therein;
    bonding the patterned surface of the second substrate to a surface of the multi-layer stack;
    thinning the first substrate; and
    removing the thinned first substrate and at least portions of the material layer to expose opposite surfaces of the membrane layer.

2. The method of claim 1, wherein the first substrate is formed of monocrystalline silicon.

3. The method of claim 2, wherein the second substrate is formed of a glass material.

4. The method of claim 3, wherein the glass material comprises fused silica, borosilicate, or a combination thereof.

5. The method of claim 3, wherein the membrane layer is formed of a dielectric material.

6. The method of claim 5, wherein the first opening has a diameter of about 100 nm or less.

7. The method of claim 6, wherein the membrane layer has a thickness of about 100 nm or less.

8. The method of claim 7, wherein bonding the patterned surface of the second substrate to the surface of the multi-layer stack includes aligning the first opening with the second opening.

9. A method of forming a flow cell, comprising:
    forming a multi-layer stack on a first substrate, the multi-layer stack comprising a membrane layer interposed between a first material layer and a second material layer, the membrane layer having a first opening formed therethrough;
    patterning a surface of a second substrate to form a second opening therein;
    bonding the patterned surface of the second substrate to a first surface of the multi-layer stack;
    removing the first substrate from the multi-layer stack to expose a second surface of the multi-layer stack opposite of the first surface;
    patterning a surface of a third substrate to form a third opening therein;
    bonding the patterned surface of the third substrate to the second surface of the multi-layer stack;
    thinning the second substrate and the third substrate to where the second opening and the third opening are respectively disposed therethrough; and
    removing at least portions of the first and second material layers to expose opposite surfaces of the membrane layer.

10. The method of claim 9, wherein the first substrate is formed of monocrystalline silicon.

11. The method of claim 10, wherein the second substrate is formed of a glass material.

12. The method of claim 11, wherein the glass material comprises fused silica, borosilicate, or a combination thereof.

13. The method of claim 11, wherein the membrane layer is formed of a dielectric material.

14. The method of claim 13, wherein the first opening has a diameter of about 100 nm or less.

15. The method of claim 14, wherein the membrane layer has a thickness of about 100 nm or less.

16. The method of claim 15, wherein bonding the patterned surface of the second substrate to the surface of the multi-layer stack includes aligning the first opening with the second opening.

17. A method of forming a flow cell, comprising:
    removing material from opposite sides of a bonded substrate, the bonded substrate comprising a first substrate and a second substrate, wherein
    a membrane layer is disposed on the first substrate, a first opening having a diameter of about 100 nm or less is formed through the membrane layer, and a material layer is disposed on the membrane layer to fill the first opening,
    the second substrate has backside surface and a patterned surface opposite the backside surface, the patterned surface has a second opening formed therein,
    the material layer of the first substrate is bonded to the patterned surface of the second substrate,
    the first opening and the second opening are aligned so that the second opening spans the first opening, and
    removing material from opposite sides of the bonded substrate comprises removing the first substrate and at least portions of the material layer and removing at least a portion of the second substrate to expose opposite surfaces of at least a portion of the membrane layer having the first opening formed therethrough.

18. The method of claim 17, wherein the first substrate is formed of monocrystalline silicon.

19. The method of claim 18, wherein the second substrate is formed of a glass material.

20. The method of claim 19, wherein the membrane layer has a thickness of about 100 nm or less.

* * * * *